United States Patent [19]

Furutani et al.

[11] Patent Number: 4,579,941

[45] Date of Patent: Apr. 1, 1986

[54] THERMALLY-DENATURED DEOXYRIBONUCLEIC ACID MD-011 AND ANTITUMOR AGENT

[75] Inventors: Yoshio Furutani; Hiroshi Yamamoto; Tamotsu Fukuda; Shizuo Shimada; Osamu Yano, all of Chiba, Japan

[73] Assignee: Mitsuitoatsu Chemicals, Inc., Tokyo, Japan

[21] Appl. No.: 407,802

[22] Filed: Aug. 13, 1982

[51] Int. Cl.$^3$ .................. C07H 15/12; C07H 17/00
[52] U.S. Cl. ............................ 536/27; 536/28; 536/29
[58] Field of Search ............................ 536/27, 28, 29

[56] References Cited

PUBLICATIONS

Chemical Abstracts 78:54332p, (1973).
Chemical Abstracts 80:13502s, (1974).
Chemical Abstracts 81:146316b, (1974).
Chemical Abstracts 86:187475z, (1977).
Chemical Abstracts 89:210828q, (1978).
Chemical Abstracts 94:119258w, (1981).
Chemical Abstracts 95:201785v, (1981).

Beerman, Biochim. Biophys. Acta, 564(3), 1979, 361–371.
Wakizawa et al., Journ. Biochem. 86(5), 1979, 1469–1478.
Millman, I. et al., "Mycobacterial Ribonucleic Acid: Comparison with Mycobacterial Cell Wall Fractions for Regression of Murine Tumor Growth", *Infection and Immunity*, pp. 929–933, Oct. 1976.
Glick, J. L. et al., "Inhibition of L1210 Tumor Growth by Thymus DNA", *Science*, vol. 149, pp. 997–998, Aug. 1965.
Glick, J. L. et al., "Specific Metabolic Changes in DNA-Treated L1210 Leukemia Cells", *Cancer Research*, vol. 27, pp. 2342–2349, Dec. 1967.
Halpern, R. M. et al., "Inhibition of Neoplastic Cell Growth by Autogenous DNA", *Proceedings of the National Academy of Science*, vol. 61, pp. 207–215, 1968.

Primary Examiner—Ethel G. Love
Attorney, Agent, or Firm—Browdy and Neimark

[57] ABSTRACT

Thermally-denatured DNA MD-011 having an antitumor activity was obtained by heating the substance separated from the disrupted cells of bacteria belonging to genus Mycobacterium.

5 Claims, 3 Drawing Figures

THERMALLY-DENATURED DEOXYRIBONUCLEIC ACID MD-011 AND ANTITUMOR AGENT

The present invention relates to a thermally-denatured deoxyribonucleic acid MD-011 (hereinafter deoxyribonucleic acid is referred to as DNA) having an antitumor activity, the DNA MD-011 being able to be obtained from bacteria belonging to genus Mycobacterium.

It is well-known that tubercle bacilli have a high antitumor and adjuvant activity. As results of research relating to cell substances with the above activities, it has higherto been reported that among the substances derived from cell wall fraction, cell wall, cell wall skeleton, water-soluble adjuvant, wax D and so on are active fractions and among the cytoplasmic arabinomannan, RNA and so on are active fractions.

From long ago the present inventors have hitherto researched for obtaining substances having an antitumor activity, said substances being derived from tubercle bacilli. In the researching process the present inventors have found the fact for the first time that a denatured DNA of tubercle bacilli have a host-mediated high antitumor activity.

Namely, by systematically researching antitumor activity as to various components of tubercle bacilli, the present inventors have obtained the following findings; a cell-free extract shows a high antitumor activity; an active fraction can be obtained as a precipitate from the cell-free extract solution by using a flocculant for nucleic acid; the antitumor activity is not lost even by heating the precipitate and the antitumor activity is rather heightened by heating. Therefore the present inventors have found the substance having the antitumor activity to be a thermally-denatured single-stranded DNA by a method comprising heating a substance obtained from the cell-free extract of tubercle bacilli by using a flocculant, said substance having the antitumor activity, and purifying the substance by a precipitation method, a column chromatography or electrophoresis and so on. The present inventors have named this thermally-denatured single-stranded DNA thermally-denatured DNA MD-011, and in this way the present invention has been completed. Hereinafter this thermally-denatured DNA MD-011 is often referred to as the thermally-denatured DNA, the DNA or the substance of the present invention.

Concerning antitumor activity of nucleic acid derived from tubercle bacilli, there is only Youmans et al's report relating to ribonucleic acid (Infection and Immunity 14, 929, 1976), and there is never any report relating to DNA yet.

The reports relating to antitumor effect of DNA derived from animal cells have being trickled from about 1965 (Science 149, 997, 1965). However, DNAs in these reports have a low antitumor activity and requires species specificity for the activity and in addition many of these DNAs lose an antitumor activity by heating. The action of these DNAs has been considered to be the following action: tumor cells may be caused to die by changing a metabolism of tumor cell or by changing a genetic control, that is to say, the action has been considered to be a direct toxic action to tumor cells (Cancer Research 27, 2342, 1967, Proceedings of the National Academy of Science 61, 207, 1968).

On the contrary the present inventors' research relating to the antitumor spectrum of the substance of the present invention gave the following results (also shown later): the substance of the present invention shows not less high an antitumor activity than the cells being starting material against tumors such as Line 10 hepatoma being an syngeneic tumor of guinea pig, IMC carcinoma, Lewis lung carcinoma (LLC), EL-4 leukemia cells and so on which are syngeneic tumors of mice; the substance of the present invention has a remarkably low toxicity and a remarkably low antigenicity. It is considered that the substance of the present invention shows the antitumor effect through an immune reaction of host, because the substance of the present invention hardly shows inhibitory effect on cell growth, even when being incubated together with tumor cells in vitro.

Further various research relating to immunological activities of the substance of the present invention gave the findings that the substance of the present invention shows an potentiating effect on killer T cell activity, an effect activating macrophage and further a remarkable effect enhancing the activity of natural killer cells. It was found by the present inventors for the first time that the thermally-denatured DNA shows the effect potentiating the activity of natural killer cell. It is considered that the effect potentiating the activity of natural killer cell provides at least one convincing basis for the action mechanism of the antitumor effect of the substance of the present invention.

And further the present inventors' research relating to the transforming abilities of the substance of the present invention against normal cells and tumor cells found that no transformation is shown in either normal cells or tumor cells under the test conditions as shown later. The substance of the present invention is derived from a microorganism cell which is extremely distinct from animal cells taxonomically. The substance of the present invention is the thermally-denatured DNA. Judging from the abovementioned points, the possibility that the substance of the present invention may show the transforming ability, is extremely low.

On the bases of the abovementioned various findings, the present inventors completed the present invention as shown hereinafter.

Namely, the present invention relates to the thermally-denatured DNA MD-011 having the antitumor activity induced by heat treatment and the salt thereof, and to be more specific, the present invention relates to the thermally-denatured DNA MD-011 having the antitumor activity, said thermally-denatured DNA MD-011 being derived from bacteria belonging to genus Mycobacterium, and the present invention relates to a process for preparing the substance of the present invention and relates to an antitumor agent.

And the present invention relates to the process for preparing the thermally-denatured DNA MD-011 having the antitumor activity, characterized in that a nucleic acid fraction is heated, said nucleic acid fraction being obtained by centrifuging disrupted cells of bacteria belonging to genus Mycobacterium.

And the present invention relates to the process for preparing the thermally-denatured DNA MD-011 having the antitumor activity, characterized in that the nucleic acid fraction is separated from a soluble fraction prepared from precipitate prepared by adding a coagulating agent for nucleic acid into the cell-free extract.

And the present invention relates to the process for preparing the thermally-denatured DNA MD-011 having the antitumor activity, characterized in that the nucleic acid fraction is separated from a supernatant solution which is obtained by subjecting the precipitate to dialyzing against water or a salt solution and then heating, said precipitate being prepared by adding the flocculant for nucleic acid into the cell-free extract.

And the present invention relates to the process for preparing the thermally-denatured DNA MD-011 having the antitumor activity, characterized in that the antitumor activity is induced by heating a material containing the DNA approximately at 80°–120° C.

And further the present invention relates to the antitumor agent comprising the thermally-denatured DNA MD-011 having the antitumor activity induced by heating as an active ingredient.

The bacteria to be used for the present invention belong to genus Mycobacterium. Among them *Mycobacterium bovis* BCG, ATCC 19015, *Mycobacterium tuberculosis* $H_{37}$Ra, ATCC 25177, *Mycobacterium smegmatis*, ATCC 607, *Mycobacterium smegmatis*, IFO 3153 and so on are enumerated as suitable bacteria.

Conventional methods may be applied for cultivating bacteria and for disrupting cells. For example, a desirable culture is prepared by using Sauton's medium or glycerine bouillon medium in the case of *Mycobacterium bovis* and so on, and by the cultivation at about 37° C. for 1–8 weeks. The cells are harvested by centrifugation or filtration of the resulting culture. The obtained cells are mixed with water, preferably a suitable buffer solution, and the resulting mixture are subjected to the disruption by Dyno-Mill or French press and so on under cooling with ice to result in providing the suspension of the disrupted cells. The cell-free extract is prepared by subjecting the obtained suspension to the centrifugation. For the centrifugation such conventional conditions as can remove undisrupted cells, partially disrupted cells, cell wall fraction and so on as a precipitate are employed satisfactorily. For example, at $5,000 \times g$ and for 10 minutes or more, the supernatant solution of the suspension is obtained.

The cell-free extract solution in the present invention means the fraction obtained by removing undisrupted cells, partially-disrupted cells, cell wall fraction and so on as much as possible from the suspension of the disrupted cells by centrifugation.

In order to obtain the nucleic acid fraction from the cell-free extract, the following methods can be employed: the nucleic acid fraction is obtained by subjecting the cell-free extract to a direct treatment with solvent (for example, Marmur's method, phenol method and so on, hereinafter such a treatment being referred to as the direct solvent method); the precipitate containing the nucleic acid fraction is obtained by adding the flocculant for nucleic acid into the cell-free extract.

The direct solvent method is suitable for obtaining the substance of the present invention on a small scale (usually 1 g or less). The nucleic acid fraction (hereinafter referred to as D nucleic acid fraction) obtained by this method usually contains impurities such as polysaccharide, protein and so on, some of said impurities having antigenicity. Therefore the substance of the present invention is obtained by removing the impurities as much as possible by a density-gradient centrifugation and so on, and then by heating the purified DNA fraction obtained after the removal of the impurities. Or the substance of the present invention is obtained by heating nucleic acid fraction D and then by removing the impurities from the heated nucleic acid fraction D by centrifugation or precipitation.

The conditions for heating nucleic acid fraction D and the purified DNA fraction are described in detail later, because the heating conditions are described also in the undermentioned explanation relating to the process for preparing the substance of the present invention.

The object of the heating in the present invention is to control the molecular weight distribution of the substance of the present invention, to increase the removal efficiency of the impurities while changing the double-stranded structure of DNA into the single-stranded structure, to make it easy to prepare the antitumor agent of the substance of the present invention, to increase the solubility for use and to obtain the substance of the present invention having a high antitumor activity and in addition a low toxicity and low side-effects.

The method, in which the flocculant for nucleic acids is added into the cell-free extract to precipitate the nucleic acid fraction, is suitable for obtaining the substance of the present invention on a large scale, because the nucleic acid fraction can be concentrated.

As the flocculant for this method any conventional flocculant are useable. However, flocculants of low molecular weight are preferable in the point that the coagulating agent used can be easily removed in the later process. As the suitable coagulating agent, polyvalent metal cations such as calcium chloride, manganese chloride, alminum sulfate and so on, and water-soluble basic antibiotics such as streptomycin, kanamycin and so on, the salts of such antibiotics and so on are enumerated. A suitable amount of the flocculant for nucleic acid may be used in compliance with its kind. For example, in the case of polyvalent metal cations 0.1–10%, preferably 0.1–3%, and in the case of antibiotics 0.01–10%, preferably 0.1–1% to the amount of the extract are suitably used.

The flocculant for nucleic acids is used as follows. The flocculant for nucleic acid is added into the cell-free extract and the resulting precipitate is separated by centrifugation or filteration to result in providing the suspension containing the nucleic acid fraction. Dialysis is preferably employed to remove the flocculant for nucleic acid from this suspension. As an aqueous solvent for dialysis, the following buffer solution is suitable: the buffer solution has an ionic strength suitable for increasing the removal efficiency of the flocculant for nucleic acid and has a pH value of around neutral. As the suitable example, phosphate buffer solution containing 0.1–1M NaCl, citrate buffer solution containing 0.1–1M KCl, carbonate buffer solution containing 0.1–1M NaCl, tris (hydroxymethyl) aminomethane buffer solution containing 0.1–1M NaCl and so on are enumerated.

The suspension containing the nucleic acid fraction is dialyzed against the buffer solution containing salt and in addition dialyzed against water to remove the salt if necessary. The dialyzed suspension containing the nucleic acid fraction is referred to as N-1 fraction hereinafter. All the operations for obtaining N-1 fraction are carried out under cooling in order to prevent an undesirable decomposition and denaturation of the nucleic acid fraction. As the cooling temperature 0°–10° C. is suitable.

In order to obtain the substance of the present invention from N-1 fraction, two methods may be employed as follows: one method is the method (A) in which the nucleic acid fraction is separated from N-1 fraction and then the obtained nucleic acid fraction is heated to provide the substance of the present invention and the other method is the method (B) in which N-1 fraction is heated and then the substance of the present invention is separated.

In the case of the former method (A), the concentration of the solute in N-1 fraction, the pH value, the concentration of the salt of the aqueous solvent and so on should be controlled first of all. The suitable concentration of the solute in N-1 fraction is 1-15 mg/ml when the soluble fraction is separated from the N-1 fraction. The suitable pH value of the aqueous solvent is in around neutral. The pH value of the aqueous solvent is usually adjusted to 5-8 with acid, alkali or a buffer solution. The ionic strength of the aqueous solvent has an influence upon the efficiency of removing the precipitate when centrifugation or other treatment is employed. The suitable ionic strength of the aqueous solvent is usually 0.1 or more. If necessary, the adjustment of ionic strength may be carried out by adding NaCl or potassium chloride.

The N-1 fraction thus regulated is centrifuged usually at 20,000×g for 5 minutes or more to provide the clear soluble fraction containing the nucleic acid as the supernatant solution. From this supernatant solution the DNA fraction can be separated by a precipitating method using streptomycin, manganese chloride or cetyltrimethylammonium bromide and so on, or by a column chromatography using Sepharose and so on, or by electrophoresis using a copolymer of vinyl chloride and vinyl acetate and so on, or by other suitable methods. All these operations are preferably carried out at 0°-10° C. Further the DNA fraction thus obtained is subjected to a heat treatment after a ribonuclease treatment, or subjected to a ribonuclease treatment after a heat treatment to provide the substance of the present invention. The conditions for the heat treatment are described later, because they are the same conditions as in the abovementioned latter method (B) for obtaining the substance of the present invention from N-1 fraction.

In the case of the latter method (B), N-1 fraction is heated first of all. The object of this heat treatment is to make the nucleic acid fraction denatured suitably and to make the impurities denatured in order to make the sequent operations for obtaining the substance of the present invention easy. There are the suitable ranges of the heat conditions, because the heat conditions have a close relationship to the antitumor activity of the substance of the present invention as described later. As factors for the heat treatment, the concentration of the solute when heating, the kind and the pH value of the aqueous solvent, the ionic strength, heating temperature and heating time are enumerated. The suitable ranges of heating conditions are as described under.

The suitable concentration of the solute is 1-15 mg/ml. In the case that the aqueous solvent is water or an aqueous solution (ionic strength: 0.1-0.5) containing a salt such as NaCl and so on, the suitable temperature is 80°-120° C. and the suitable time is 5-120 minutes. In the case that the aqueous solvent is a buffer solution, the heating conditions are influenced greatly by the pH value of the buffer solution, and therefore in the case of a pH value of around neutral, a high heating temperature and long heating time are suitable, and in the case of an acid or alkaline pH value, a low heat temperature and short heating time are suitable.

Employing the suitable heating conditions as mentioned above can provide the suspension containing the thermally-denatured DNA having a high antitumor activity intended by the present invention and a low antigenicity as described later.

The abovementioned heating conditions are important factors for the process for preparing the substance of the present invention, and are applicable to all the processes as shown in the present specification.

In this way, N-1 fraction is heated and cooled and then subjected to the removal of the precipitate by centrifugation or filteration and so on to provide the clear solution containing the substance of the present invention. From this solution the substance of the present invention is easily separated by conventional methods, and as the suitable examples there are the precipitation method using the flocculant for nucleic acid, the fractionation method using an organic solvent, the column chromatography, the electrophoresis and so on, and the combination of each above-enumerated method with ribonuclease treatment and so on. The substance of the present invention which is obtained by such a method can be used as an active ingredient of antitumor agent as it is, or can be subjected to lyophilization to provide the dry powder.

Molecular weight of DNA of the substance of the present invention shows the distribution of approximately 30,000-1,000,000, and the total amount of guanine and cytosine is about 60%. The substance of the present invention does not show a clear transition temperature. When the substance of the present invention is fractionated by the chromatography on the column of hydroxyapatite for nucleic acids, the substance of the present invention proves to be the single-stranded DNA.

The substance of the present invention, which is obtained by the processes as shown in the present specification, contains extremely small impurities such as RNA, protein, polysaccharide and so on in some cases. However, these impurities are, so to speak, in a trace amount or so. These impurities can be removed by a purification procedure.

The physicochemical properties of M-5 obtained in Example 5 were examined. The results are shown as follows. M-1, M-2, M-3, M-4 and M-6 obtained respectively in Example 1, 2, 3, 4 and 6 showed the same physicochemical properties as in M-5.

Figure 1:
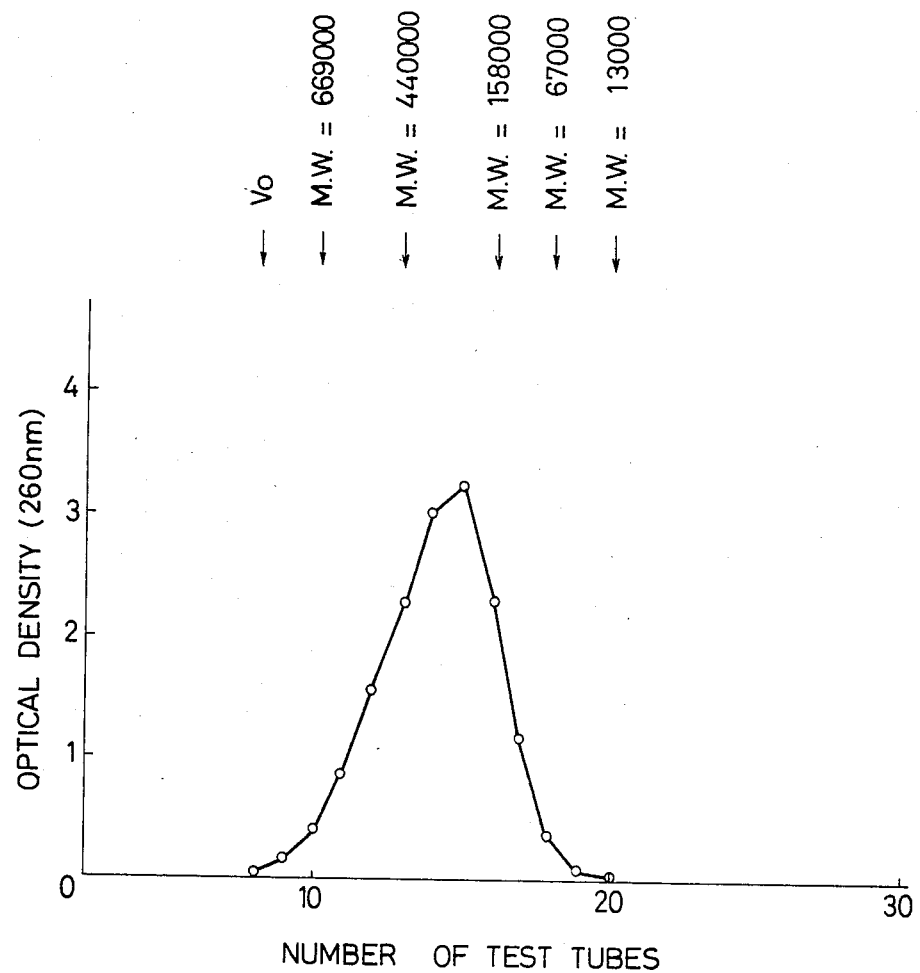
FIG. 1 shows the elution pattern of the substance of the present invention by the column chromatography of Sepharose.
Figure 2:
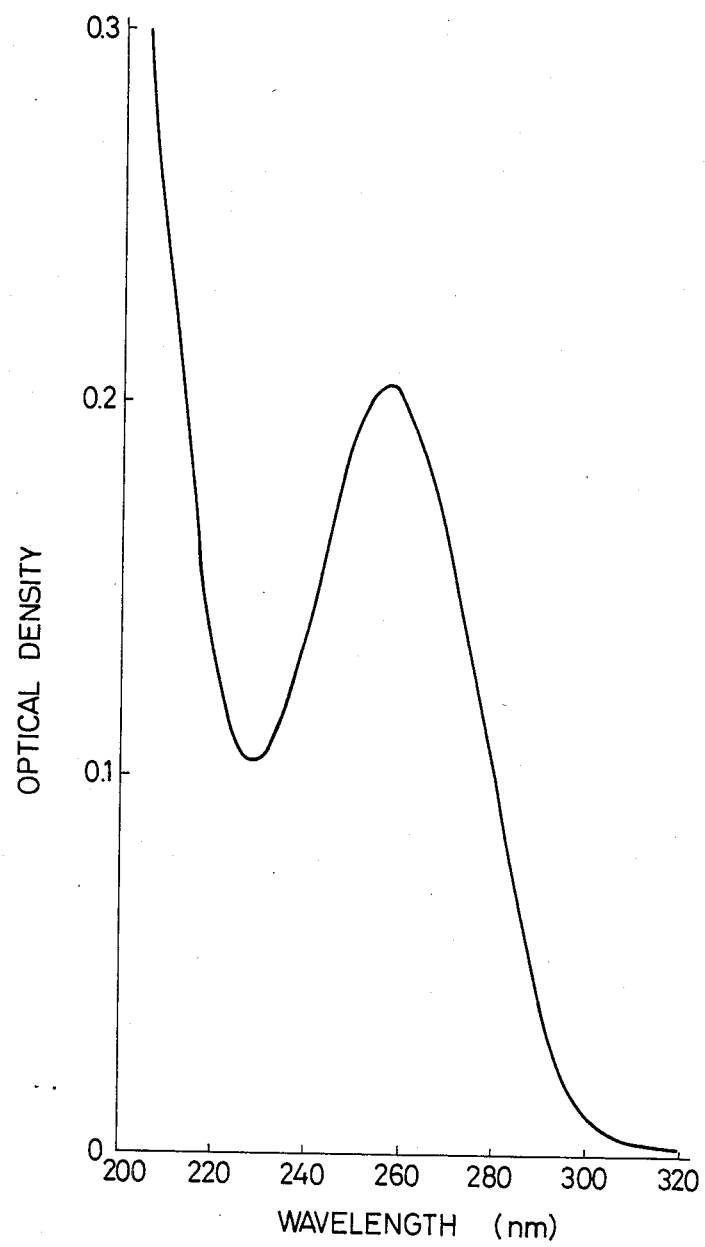
FIG. 2 shows the UV absorption spectrum of the substance of the present invention.
Figure 3:
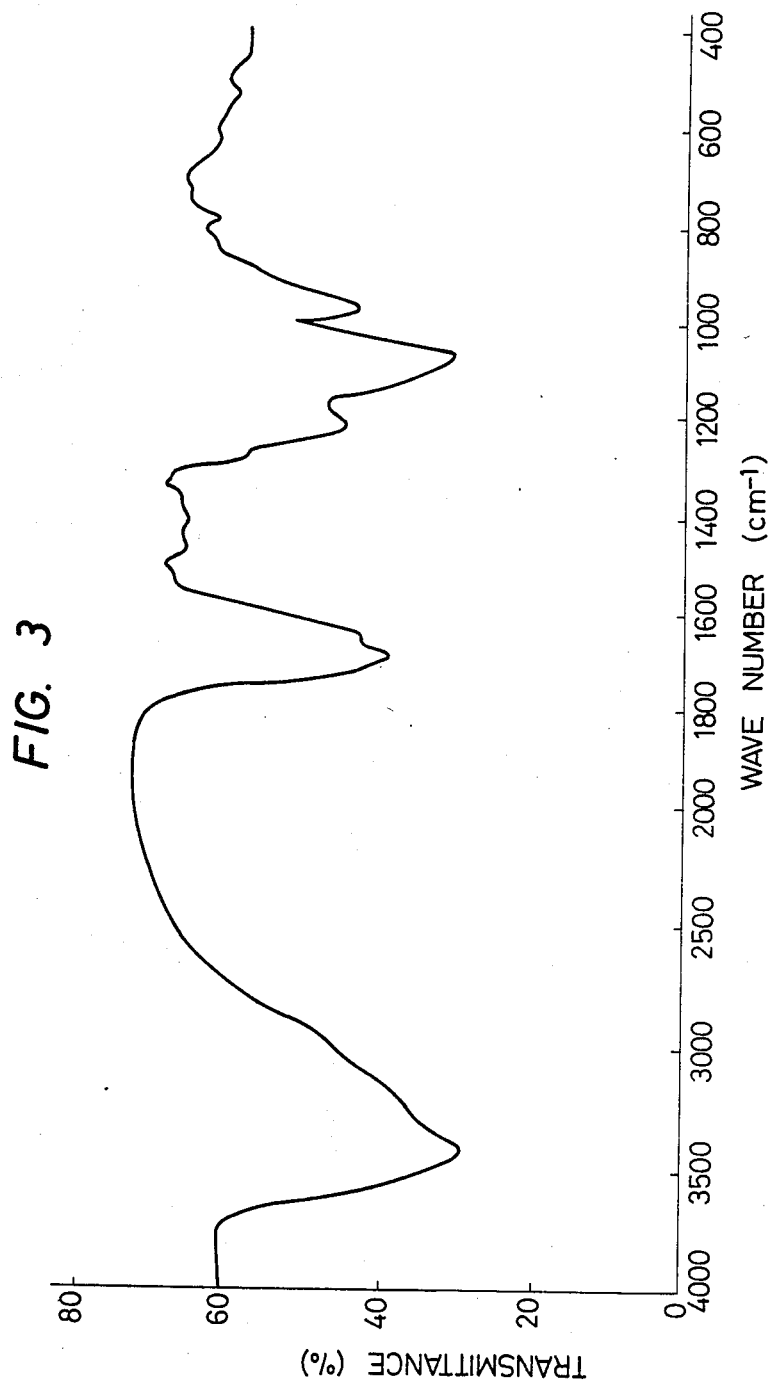
FIG. 3 shows the IR absorption spectrum of the substance of the present invention.

The physicochemical properties (as the sodium salt) of the substance of the present invention, that is to say, the thermally-denatured DNA MD-011:
(1) Element analysis: C: 25.57–30.75, H: 3.80–4.75, N: 12.67–14.36, P: 7.30–8.59, Na: 3.59–5.0
(2) Molecular weight: 30,000–1,000,000 (Molecular weight distribution pattern As shown in FIG. 1)
(3) Melting point: The sodium salt does not show a clear melting point.
(4) UV absorption spectrum As shown in FIG. 2
(5) IR absorption spectrum As shown in FIG. 3
(6) Solubilities in solvents: soluble in water, insoluble in ethanol, methanol, ether or acetone
(7) Color reaction:

(i) Orcinol reaction: negative to RNA fraction obtained by STS fractionation method
(ii) Diphenylamine reaction: positive to DNA fraction obtained by STS fractionation method
(iii) Ninhydrin reaction: negative in a concentration of 10 μg/ml
(iv) Anthrone reaction: negative in a concentration of 10 μg/ml
(8) Basicity, acidity or neutrality: Aqueous solution of the sodium salt shows a pH value of 6.5–7.5.
(9) Color: white powder
(10) Specific properties: In this invention dissolvability and a high antitumor activity are provided by heating, and toxicity and antigenicity are extremely lowered by heating.
(11) Base composition: guanine: 30.4, adenine: 16.9, cytosine: 30.8, thymine: 21.9 (obtained by chemical analysis)
(12) Enzyme treatment: Antitumor activity is lost by treating with deoxyribonuclease I (DNase I). Antitumor activity is not changed by treating with ribonuclease $T_2$ (RNase $T_2$).
(13) Column chromatography: Fractionation by chromatography on a column of hydroxyapatite for analyzing nucleic acids shows single-stranded structure.
(14) Transition temperature (Tm): A clear transition temperature is not able to be determined.

The substance of the present invention loses the antitumor activity by treating with deoxyribonuclease (DNase I) and does not change the antitumor activity by treating with ribonuclease (RNase $T_2$). Therefore the entity relating to the antitumor activity which the substance of the present invention shows, proves to be the thermally-denatured DNA.

For using the substance of the present invention as the antitumor agent, an agent for injection is suitable. The substance of the present invention can be used alone, or together with a conventional pharmaceutically acceptable carrier for a liquid agent or lyophilized agent. As the pharmaceutically acceptable carrier, mannitol, sorbitol, maltose, dextran, squalene, and so on are enumerated.

The substance of the present invention can be used for an emulsion-type agent of oil-in-water or water-in-oil.

In the case of the substance of the present invention, the dose to be used for the antitumor agent and the administration route can be fittingly selected. The suitable dose of the substance of the present invention is 0.01–100 mg/kg-body weight. Intradermal, subcutaneous, intravenous, intraperitoneal, peroral, or intratumoral administration is fittingly employed.

The substance of the present invention shows a high antitumor effect against various tumors of guinea pigs and mice. For example, in the cases of IMC carcinoma, Lewis lung carcinoma (LLC), EL-4 leukemia, P-815 mastocytoma and so on which are syngeneic tumors of mice, the substance of the present invention showed not less high an antitumor activity than the cells being the starting material in both points of the suppressive and regressive activity: the suppressive activity is tested by inoculating into an animal flank the mixture of the physiological saline solution of the substance of the present invention with tumor cells; the regressive activity is tested by administering the substance of the present invention directly into the tumor lesion. In the case of Line 10 being an syngeneic tumor of guinea pigs, the water-in-oil emulsion of the substance of the present invention showed not only the growth inhibition activity against the primary tumor but also the inhibition activity against the metastasis of the tumor to the regional lymph node.

Further the physiological saline solution of the substance of the present invention showed the antitumor activity against IMC carcinoma, even when the administration was carried out into a place apart from IMC tumor lesion.

The acute toxicity of the substance of the present invention is extremely low, because 50% lethal dose ($LD_{50}$) in mice is 1 g or more/kg-body weight in the case of the intraveneous administration.

And the substance of the present invention proved to be remarkably safe also in terms of antigenicity by anaphylaxis test and delayed-type allergy test carried out by using guinea pigs.

Further the following points were made clear by various tests: pyrogenicity, pain induction, inflammation induction, granuloma formation and so on of the substance of the present invention are extremely lower than those of cells being the starting material and are on such levels that the substance of the present invention is useful as an usual medicine.

Cell growth inhibitions by the substance of the present invention against the cells of various tumors were examined and however hardly detected. Therefore it was considered that the substance of the present invention may show the antitumor activity through the immune reaction of the host, and then the immunological activities of the substance of the present invention were examined in various ways. Consequently, the substance of the present invention showed an effect potentiating killer T cell activity, an effect activating macrophage and an effect enhancing the activity of natural killer cell.

Further the present inventors examined whether the transforming abilities against normal cells and tumor cells were showed or not by the substance of the present invention, because the substance of the present invention is DNA being a genetic factor though it is the thermally-denatured DNA. The possibility of transformation by the substance of the present invention is considered to be extremely low in consideration of the results shown later.

On the bases of the abovementioned various findings, the substance of the present invention is judged to be remarkably useful as an antitumor agent for various tumors such as malignant melanoma, lung cancer, stomach cancer, bowel cancer, colorectal cancer, leukemia, prostatic cancer, breast cancer, sarcoma and so on.

Hereinafter the processes for preparing the substance of the present invention are shown in Examples and the values of the substance of the present invention as the antitumor agent are shown in Tests.

EXAMPLE 1

The preparation of the substance of the present invention by Marmur's method:

One liter of glycerine bouillon medium was made by adding water to the mixture of 50 ml of glycerine, 2 g of citric acid, 15 g of meat extract, 0.05 g of ammonium citrate, 1 g of $K_2HPO_4$ and 1 g of $MgSO_4.7H_2O$, and by adjusting the pH value to 7.0–7.2.

In glycirine bouillon medium having the abovementioned composition, *Mycobacterium bovis* BCG, ATCC 19015 was subjected to the cultivation at 37° C. for 3 weeks. The obtained culture was centrifuged to provide 500 g of the wet cells. 500 g of the wet cells was suspended into 10 mM phosphate buffer (pH 7.0) solution of the volume of 7 times the wet cells used and the resulting suspension was subjected to the disruption by Dyno-Mill under cooling with ice and then centrifuged at 20,000×g for 20 minutes to provide the cell-free extract. From this extract the crude DNA fraction was obtained by Marmur's method (Marmur, Journal of Molecular Biology 3, 208, 1961). By applying this fraction on the column of Sepharose 6B (Pharmacia Fine Chemicals Co.), the DNA fraction was obtained as a fraction of void volume. The DNA fraction thus obtained was concentrated and then purified by the density-gradient centrifugation using cesium chloride to provide the half-purified DNA fraction. This fraction was dialyzed, and into the dialyzed fraction was added NaCl in such an amount that the final concentration would be 0.9%, and the obtained solution was heated at 100° C. for 60 minutes. The heat-treated fraction was cooled and dialyzed against a distilled water and then lyophilized to provide 8.4 mg of the dry material. Then, 8.4 mg of the dry material was dissolved into 2.0 ml of 0.05M acetate buffer solution (pH 4.5) and thereinto 20 U of ribonuclease $T_2$ (Sankyo Co.) was added. This enzyme treatment was carried out at 37° C. for 22 hours. Into the reaction mixture was added the mixture of chloroform and isoamyl alcohol (24:1, V/V) in the same amount as the amount of the reaction mixture, and the obtained solution was shaken and then centrifuged to provide the water phase. The total amount of the water phase was applied on the column (diameter: 1.0 cm, length: 20 cm) charged with Sephadex G 100 (Pharmacia Fine Chemicals Co.) which had been equilibriated with 0.05M ammonium bicarbonate solution, and then the elution was carried out by using the same buffer solution to provide the fraction containing DNA as the fraction of void volume. This fraction was dialyzed against water and neutralized with a sodium hydroxide solution and then lyophilized to provide 5.6 mg of the substance of the present invention. The substance thus obtained of the present invention is referred to as M-1 hereinafter.

The DNA content of M-1 was 97.5% when the quantitative analysis was carried out by diphenylamine method (Biochemical Journal 62, 315, 1956) after hydrolysis with 5% perchloric acid.

EXAMPLE 2

Preparation of the substance of the present invention from the soluble fraction of the suspension obtained by using streptomycin:

*Mycobacterium bovis* BCG, ATCC 19015 was subjected to the cultivation at 37° C. for 3 weeks in the same glycerine bouillon medium as in Example 1. The obtained culture was centrifuged to provide 3.3 kg of wet cells. Then, 3.3 kg of the wet cells was suspended into 10 mM phosphate buffer solution (pH 7.0) of the amount of 7 times the wet cells used, and the resulting suspension was subjected to the disruption by Dyno-Mill under cooling with ice and then centrifuged at 20,000×g for 20 minutes to provide 21 l of the cell-free extract. Into this extract solution was added 63 g of streptomycin sulfate, and the obtained solution was stirred sufficiently and thereafter allowed to stand at 4° C. overnight. The resulting precipitate was collected by centrifugation and suspended into 10 mM phosphate buffer solution (pH 7.0) containing 0.5M NaCl. This suspension was packed into a cellophane tube and dialyzed against the same buffer solution as above and in addition dialyzed against a distilled water to provide 8 l of the suspension containing the nucleic acid fraction (this suspension is referred to as NB-1 hereinafter). The solid concentration of NB-1 was 10 mg/ml and the yield was 12% in terms of the dried cells.

Next, into 200 ml of NB-1 was added 200 ml of 1.8% NaCl solution, and the resulting solution was stirred and then centrifuged at 20,000×g for 30 minutes to provide the supernatant solution. NaCl was added to this supernatant solution in such an amount that the final concentration would be 0.4M and dissolved. Into the obtained solution was added cetyltrimethylammonium bromide (hereinafter referred to as CTAB, Tokyo Kasei Kogyo Co., Ltd.) in such an amount that the final concentration would be 0.2% (w/v), and the resulting solution was stirred sufficiently and thereafter allowed to stand at room temperature for 30 minutes. The resulting precipitate was collected by centrifugation and dissolved into 60 ml of 1M NaCl solution. Into the obtained solution was added the mixture of chloroform and isoamyl alcohol (24:1, V/V) in the same amount as the amount of the obtained solution, and the resulting solution was shaken and then centrifuged to provide the water phase. In addition this treatment was repeated twice. Into the obtained water phase was added 99.5% ethanol in a volume of 3 times the water phase obtained, and the obtained solution was stirred and thereafter allowed to stand at 4° C. overnight. The resulting precipitate was collected by centrifugation and dissolved into a distilled water and then dialyzed against a distilled water to provide the purified nucleic acid solution. Into this solution was added NaCl in such an amount that the final concentration would be 0.9%, and the obtained solution was heated at 100° C. for 60 minutes and dialyzed against a distilled water and then lyophilized to provide 93 mg of the dry material. Then 93 mg of the dry material was dissolved into 10 ml of 0.05M acetate buffer solution (pH 4.5) and thereinto was added a solution of 200 U of ribonuclease $T_2$ (Sankyo Co.) in 2 ml of the above buffer solution. This enzyme treatment was carried out at 37° C. for 22 hours. Into the reacted solution was added the mixture of chloroform and isoamyl alcohol (24:1, V/V) in the same volume as the volume of the reaction mixture, and the resulting solution was shaken and then centrifuged to provide the water phase. The total water phase was applied on the column (diameter: 2.5 cm, length: 90 cm) of Sephadex G 100 (Pharmacia Fine Chemicals Co.) which had been equilibriated with 0.05 M ammonium bicarbonate solution, and then the elution was carried out by using the same buffer solution to provide the fraction containing DNA as the fraction of void volume. This fraction was dialyzed against water and neutralized by a sodium hydroxide solution and then lyophilized to provide 62 mg of the substance of the present invention. The substance thus obtained of the present invention is referred to as M-2 hereinafter.

The DNA content of M-2 proved to be 97.0% by the same analysis as in Example 1.

EXAMPLE 3

Preparation of the substance of the present invention from the soluble fraction derived from *Mycobacterium smegmatis*:

*Mycobacterium smegmatis*, ATCC 607 was subjected to the cultivation at 37° C. for 4 weeks in the same glycerine bouillon medium as in Example 1. The obtained culture was centrifuged to provide 500 g of wet cells. Five hundred grams of the wet cells was treated in the same manner as in Example 2 to provide 1 l of the suspension containing the nucleic acid fraction. The solid concentration of this suspension was adjusted to 10 mg/ml by adding water. At this time the yield was 15% in terms of the dried cells. This suspension is referred to as NS-1 hereinafter. NS-1 was treated in the same manner as after obtaining NB-1 in Example 2 to provide 77 mg of the substance of the present invention. This substance of the present invention is referred to as M-3 hereinafter.

EXAMPLE 4

Preparation of the substance of the present invention from the heated supernatant solution by electrophoresis:

Into 1 l of NB-1 obtained in Example 2 was added 1 l of 1.8% NaCl solution, and the obtained solution was stirred sufficiently and heated at 100° C. for 60 minutes and then centrifuged at $10,000 \times g$ for 20 minutes to provide the supernatant solution (this supernatant solution is referred to as S-3 hereinafter). S-3 was dialyzed against a distilled water and lyophilized to provide 44 mg of the dry material. Forty-four milligrams of the dry material was dissolved into 0.05 M borate buffer solution (pH 7.4) and subjected under cooling to the electrophoresis using the copolymer of vinyl chloride and vinyl acetate (BDH Chemicals Co.) as a carrier. After electrophoresis, the copolymer was cut and taken out as the block having a width of 1 cm and subjected to the elution using 0.1 M NaCl solution to collect the fraction by UV absorption at 260 nm. The obtained fraction was dialyzed against a distilled water and lyophilized to provide 19 mg of the dry material. Next, 19 mg of the dry material was dissolved into 2.0 ml of 0.05 M acetate buffer solution (pH 4.5) and thereinto 40 U of ribonuclease $T_2$ (Sankyo Co.) was added. This enzyme treatment was carried out at 37° C. for 22 hours. Into the reaction mixture was added the mixture of chloroform and isoamyl alcohol with 24:1 ratio in the same volume as the volume of the reaction mixture, and the resulting solution was shaken and centrifuged to provide the water phase. The total amount of the water phase was applied on the column (diameter: 1.0 cm, length: 20 cm) of Sephadex G 100 (Pharmacia Fine Chemicals Co.) which had been equilibriated with 0.05 M ammonium bicarbonate solution, and then the elution was carried out by using the same buffer solution to provide the fraction containing DNA as the fraction of void volume. This fraction was dialyzed against water and neutralized with a sodium hydroxide solution and then lyophilized to provide 13.1 mg of the substance of the present invention. The thus obtained substance of the present invention is referred to as M-4.

The DNA content of M-4 proved to be 98.4% by the same analysis as in Example 1.

EXAMPLE 5

Preparation of the substance of the present invention from the heated supernatant solution derived from BCG bacteria by using CTAB:

Into 1 l of NB-1 obtained in Example 2 was added 1.8% NaCl solution in the same amount. The obtained solution was stirred and heated at 100° C. for 60 minutes and cooled and then centrifuged at $10,000 \times g$ for 20 minutes to provide the supernatant solution. The supernatant solution was added with NaCl in such an amount that the final concentration would be 0.4 M and stirred, and added with CTAB in such an amount that the final concentration would be 0.2% (w/v) and stirred sufficiently, and then allowed to stand at room temperature for 30 minutes. The resulting precipitate was collected by centrifugation and dissolved into 400 ml of 1 M NaCl solution. The obtained solution was subjected to the same organic solvent treatment and precipitation treatment by ethanol as in Example 2. The treated solution was dialyzed against a distilled water and lyophilized to provide 1.04 g of the dry material. This dry material is referred to as C-B-1 hereinafter.

The DNA content of C-B-1 proved to be 86.6% by the same analysis as in Example 1.

Further C-B-1 was treated with ribonuclease $T_2$ in the same scale as in Example 2 and purified to provide 70 mg of the substance of the present invention. This substance of the present invention is referred to M-5 hereinafter.

The DNA content of M-5 proved to be 99.6% by the same analysis as in Example 1.

EXAMPLE 6

Preparation of the substance of the present invention from the heated supernatant solution derived from *Mycobacterium tuberculosis*:

One liter of Modified Sauton's medium was made by adding water into the mixture of 50 ml of glycerine, 2 g of citric acid, 2 g of L-aspartic acid, 0.05 g of ammonium iron citrate, 1 g of $K_2HPO_4$, 1 g of $MgSO_4.7H_2O$, 0.01 g of $ZnSO_4.7H_2O$, 0.5 mg of $CaCl_2.2H_2O$, and 0.1 mg of $CuSO_4.5H_2O$, and by adjusting a pH value to 7.0–7.2.

In modified Sauton's medium having the abovementioned composition, *Mycobacterium tuberculosis* $H_{37}Ra$, ATCC 25177 was subjected to the cultivation at 37° C. for 4 weeks. Into the obtained culture mixture was added phenol in such an amount that the final concentration would be 5%. The obtained mixture was stirred and allowed to stand overnight and then centrifuged to provide wet cells. The collected wet cells were washed with physiological saline. One hundred grams of the washed wet cells was treated in the same manner as in the preparation of NB-1 in Example 2 to provide 200 ml of the suspension containing the nucleic acid fraction. After adjustment of the solid concentration of this suspension to 10 mg/ml, the suspension was treated in the same manner as in the preparation of M-5 in Example 5 to provide 205 mg of the substance of the present invention. This substance of the present invention is referred to as M-6 hereinafter.

The DNA content of M-6 proved to be 96.3% by the same analysis as in Example 1.

EXAMPLE 7

Liquid agent:

Ten milligrams of M-5 was dissolved into 10 ml of PBS (−) solution (EIKEN CHEMICAL Co., Ltd.). The solution was subjected to the aseptic filtration using Nuclepore-NO 20 (Nuclepore Co.). The obtained filtrate was aseptically poured into each vial bottle in an volume of 1.5 ml to provide the liquid agent of the substance of the present invention.

EXAMPLE 8

Lyophilized agent:

Ten milligrams of M-5 was dissolved into 10 ml of the distilled water for injection. Into the solution was added 500 mg of maltose and dissolved. The obtained solution was subjected to the aseptic filtration using Nuclepore-NO 20. The obtained filtrate was aseptically poured into each vial bottle in an amount of 1 ml and lyophilized to provide the lyophilized agent of the substance of the present invention.

EXAMPLE 9

Emulsion-type agent:

Four milligrams of M-5 was dissolved into 0.5 ml of physiological saline. Into the resulting solution was added 0.5 ml of the mixture of Drakeol 6-VR (Pensilvania Refining Co.) and Arlacel A (Atlas Chemical Industries Co.) with 8.5:1.5 ratio to provide the water-in-oil emulsion.

TEST 1

Antitumor effect against mouse IMC carcinoma:

The antitumor effect of the substance of the present invention was tested against IMC carcinoma.

The test was carried out as follows:

$CDF_1$ female mice were used. Half a million IMC carcinoma cells were inoculated intradermally. On alternate days starting on the 1 day after the inoculation, day after the inoculation, the agent prepared in the same manner as shown in Example 7 was administered into tumor 6 times (in total) in an volume of 0.1 ml per once. On the 35th day after the inoculation, the tumor was excised and weighed.

The results are shown in Table 1.

TABLE 1

Antitumor effect against IMC carcinoma:

| No. | Sample | Dose per injection (μg) | Average tumor weight (g ± SD) | T/C (%) | No. of mice cured/ No. of mice tested |
|---|---|---|---|---|---|
| 1 | Control | 0 | 2.84 ± 0.70 | 100 | 0/10 |
| 2 | M-1 | 100 | 0.28 ± 0.53* | 10 | 7/10* |
| 3 | M-2 | 100 | 0.22 ± 0.23* | 8 | 7/10* |
| 4 | M-4 | 100 | 0 | 0 | 10/10* |
| 5 | C-B-1 | 100 | 0.01 ± 0.02* | 0 | 8/10* |
| 6 | M-5 | 100 | 0* | 0 | 10/10* |
| 7 | M-6 | 100 | 0.01 ± 0.03* | 0 | 8/10* |
| 8 | BCG | 100 | 1.05 ± 1.10* | 37 | 1/10 |

*p < 0.01

For analysis of significant differences in average tumor weight and incidence of cured mice, Student's t-test and Fischer's test were employed respectively hereinafter. T/C means the ratio (%) of the average tumor weight of the agent group to the average tumor weight of the control group. BCG vaccine (JAPAN BCG LABORATORY) was used as BCG. Physiological saline was used as a control.

TEST 2

Antitumor effect against Meth A fibrosarcoma:

The antitumor effect of the substance of the present invention was tested against Meth A fibrosarcoma.

The test was carried out as follows:

BALB/C female mice were used. Two hundred thousand Meth A fibrosarcoma cells were inoculated intradermally into the flank of the mice. Twice a week from the 4th day after the inoculation, the agent prepared in the same manner as shown in Example 7 was administered into tumor lesion 6 times (in total) in an volume of 0.1 ml per once. On the 25th day after the inoculation, the tumor was excised and weighed.

The results are shown in Table 2.

TABLE 2

Antitumor effect against Meth A fibrosarcoma of mouse:

| No. | Sample | Dose per injection (μg) | Average tumor weight (g ± SD) | T/C (%) | No. of mice cured/ No. of mice tested |
|---|---|---|---|---|---|
| 1 | Control | 0 | 0.97 ± 0.65 | 100 | 0/9 |
| 2 | M-5 | 100 | 0* | 0 | 8/8* |
| 3 | BCG | 100 | 0.08 ± 0.11* | 8 | 3/8 |

*p < 0.01

Physiological saline was used as a control. BCG vaccine (JAPAN BCG LABORATORY) was used as BCG.

TEST 3

Antitumor effect against mouse Lewis lung carcinoma:

The antitumor effect of the substance of the present invention was tested against Lewis lung carcinoma.

The test was carried out as follows:

C57BL/6 female mice were used. Half a million Lewis lung carcinoma cells were inoculated intradermally. On the 1st, 4th, 8th, 11th, 15th and 18th days after the inoculation, the agent prepared in the same manner as shown in Example 7 was administered into tumor lesion in an volume of 0.1 ml per once. On the 26th day after the inoculation, the tumor was excised and weighed. In addition the number of pulmonary metastasis was counted.

The results are shown in Table 3.

Physiological saline was used as a control. BCG vaccine (JAPAN BCG LABORATORY) was used as BCG.

TABLE 3

| No. | Sample | Dose per injection (μg) | No. of mice cured/ No. of mice tested | Average tumor weight (g ± SD) | T/C (%) | Average number of metastasis per one mouse | T/C (%) |
|---|---|---|---|---|---|---|---|
| 1 | Control | 0 | 0/8 | 3.34 ± 0.88 | 100 | 35.1 ± 8.9 | 100 |
| 2 | C-B-1 | 100 | ⅛ | 1.42 ± 0.91** | 42.5 | 6.3 ± 6.4** | 17.9 |
| 3 | C-B-1 | 250 | 4/8 | 1.20 ± 1.32** | 35.9 | 7.0 ± 8.2** | 19.9 |
| 4 | C-B-1 | 500 | 4/8 | 0.85 ± 0.93** | 25.4 | 5.2 ± 7.3** | 14.8 |
| 5 | M-5 | 500 | ⅝ | 0.75 ± 0.82** | 22.4 | 5.5 ± 6.2** | 15.6 |
| 6 | BCG | 100 | 0/8 | 4.78 ± 1.08* | 143.1 | 11.1 ± 11.0** | 31.6 |
| 7 | BCG | 500 | 0/8 | 3.75 ± 2.19 | 112.3 | 8.0 ± 8.8** | 22.8 |

*p < 0.05,
**p < 0.01

TEST 4

Antitumor effect against mouse EL-4:

The antitumor effect of the substance of the present invention was tested against mouse EL-4.

The test was carried out as follows:

C57BL/6 female mice were used. Half a milliliter of Hanks' balanced salt solution in which 1×10⁶/ml EL-4 leukemia cells had been suspended was mixed with 0.5 ml of physiological saline solution in which the agent had been dissolved in an concentration of 2 mg/ml. A 0.1-ml portion of the obtained mixture was inoculated intradermally. On the 37th day after the inoculation, mean survival times of the mice were determined.

By using only physiological saline, the physiological saline was treated as a control in the same manner. BCG vaccine (JAPAN BCG LABORATORY) was used as BCG.

The results are shown in Table 4.

TABLE 4

Antitumor effect against mouse EL-4:

| No. | Sample | Dose (μg) | No. of mice surviving/No. of mice tested |
|---|---|---|---|
| 1 | Control | 0 | 0/10 |
| 2 | C-B-1 | 100 | 0/10 |
| 3 | C-B-1 | 200 | 1/10 |
| 4 | C-B-1 | 400 | 4/10* |
| 5 | C-B-1 | 800 | 9/10** |
| 6 | M-3 | 400 | 4/10* |
| 7 | M-5 | 400 | 5/10* |
| 8 | M-5 | 800 | 9/10** |
| 9 | BCG | 400 | 1/10 |

*$p < 0.05$,
**$p < 0.01$

TEST 5

Antitumor effect against Line 10 hepatoma of guinea pigs (Strain 2):

The antitumor effect of the substance of the present invention was tested against Line 10 hepatoma of guinea pigs (Strain 2).

One million Line 10 hepatoma cells were inoculated intradermally. On the 7th day after the inoculation, 0.1 ml of the agent prepared in the same manner as shown in Example 9 was administered into tumor lesion. On 80th day after the inoculation, the number of surviving animals, the number of animals cured, and the number of animals with metastasis to the regional lymph node were examined. As a control the physiological saline was treated in the same manner.

The results are shown in Table 5.

TABLE 5

Antitumor effect against Line 10 hepatoma of guinea pig (Strain 2):

| No. | Sample | Dose (μg) | No. of animals cured/No. of animals tested | No. of animals with no metastasis/No. of animals tested | Mean survival days |
|---|---|---|---|---|---|
| 1 | Control | 0 | 0/6 | 0/6 | 46.2 ± 2.6 |
| 2 | M-4 | 400 | 4/6 | 4/6 | 79.5 ± 3.5** |
| 3 | C-B-1 | 400 | 6/6 | 6/6 | >80** |
| 4 | M-5 | 400 | 6/6 | 6/6 | >80** |

**$p < 0.01$

TEST 6

Antitumor effect of the nuclease-treated material:

By treating the substance of the present invention with nuclease, the entity of the antitumor activity of the substance of the present invention was examined.

The test was carried out as follows:

C-B-1 and M-5 were treated with deoxyribonuclease (DNase I, Sigma Chemicals Co.) or ribonuclease (RNase T₂, Sigma Chemicals Co.) to provide each decomposed material. The decomposed material was treated with chloroform to remove DNase I or RNase T₂ and desalted by using the column of Sephadex G 10 (Farmacia Fine Chemicals Co.) and then lyophilized to provide the nuclease-treated material of the substance of the present invention. The antitumor activity of this material was tested in the same manner as in Test 1.

The results are shown in Table 6-1 and Table 6-2.

TABLE 6-1

Antitumor effect of the nuclease-treated material against IMC carcinoma (1):

| No. | Sample | Dose per injection (μg) | Average tumor weight (g ± SD) | T/C (%) | No. of mice cured/No. of mice tested |
|---|---|---|---|---|---|
| 1 | Control | 0 | 3.82 ± 1.55 | 100 | 0/10 |
| 2 | C-B-1 | 100 | 0.13 ± 0.35** | 3 | 8/10** |
| 3 | C-B-1 DNase | 100 | 2.28 ± 0.74* | 60 | 0/10 |
| 4 | C-B-1 RNase | 100 | 0.11 ± 0.23** | 3 | 8/10** |
| 5 | RNase" | 0.5 U | 2.98 ± 1.22 | 78 | 0/10 |
| 6 | BCG | 100 | 0.47 ± 0.76** | 12 | 1/10 |

*$p < 0.05$,
**$p < 0.01$
": The amount of RNase was equivalent to that of RNase used to 100 μg of C-B-1.

TABLE 6-2

Antitumor effect of the nuclease-treated material against IMC carcinoma (2):

| No. | Sample | Dose per injection (μg) | Average tumor weight (g ± SD) | T/C (%) | No. of mice cured/No. of mice tested |
|---|---|---|---|---|---|
| 1 | Control | 0 | 3.12 ± 1.01 | 100 | 1/10 |
| 2 | M-5 | 100 | 0* | 0 | 10/10* |
| 3 | M-5 RNase | 100 | 0* | 0 | 10/10* |
| 4 | M-5+" DNase | 100 | 2.25 ± 1.86 | 72 | 0/10 |

*$p < 0.01$
": The mixture obtained by treating M-5 with DNase was administered as it was. The dose of a injection was equivalent to 100 μg of M-5.

T/C means the ratio (%) of the average tumor weight of the agent group to the average tumor weight of the control group. Physiological saline was used as the control. BCG vaccine (JAPAN BCG LABORATORY) was used as BCG.

TEST 7

Potentiating effect on the activity of natural killer cell (NK cell):

The potentiating effect of the substance of the present invention was tested against natural killer cell.

The test was carried out as follows:

C57BL/6 female mice (8 weeks of age) were used. The following three agents were used: physiological saline; physiological saline solution in which C-B-1 had been dissolved in a concentration of 1 mg/ml; physiolgical saline solution in which M-5 had been dissolved in a concentration of 1 mg/ml. The agent was administered intraperitoneally in a volume of 0.3 ml/mouse. Forty-eight hours after the administration, the peritoneal exudate cells were harvested. The number of peritoneal exudate cells was adjusted to 2×10⁶/ml by using RPMI 1640 medium supplemented with 10% fetal calf serum. The cell suspension was seeded into plastic petri dish and subjected to the incubation in the air containing 5%

$CO_2$ at 37° C. for 90 minutes to provide adherent cells and non-adherent cells.

Half a million adherent or non-adherent cells were incubated with $^{51}Cr$-labelled YAC-1 leukemia cells at 37° C. in the air containing 5% $CO_2$ for 4 hours by using RPMI 1640 medium supplemented with 10% fetal calf serum. The radioactivity of $^{51}Cr$ released in the supernatant of the culture was measured by auto gamma counter (Packard Co.) to detect the cytotoxic effect of the peritoneal exudate cells against YAC-1 cells.

The results are shown in Table 7.

TABLE 7

| Potentiating effect on the activity of NK cell: | | |
|---|---|---|
| Sample | | % release of $^{51}Cr$ (%) |
| Physiological saline, | Non-adherent cells | 15.6 |
| Physiological saline, | Adherent cells | 1.8 |
| C-B-1, | Non-adherent cells | 40.1 |
| C-B-1, | Adherent cells | 3.6 |
| M-5, | Non-adherent cells | 46.2 |
| M-5, | Adherent cells | 2.1 |

TEST 8

Direct inhibitory effect against cell growth:

The direct inhibitory effect of the substance of the present invention was tested against the cell growth of YAC-1 mouse leukemia cell, mouse FM3A mammary cancer cell or mouse Meth A fibrosarcoma cell.

The test was carried out as follows:

YAC-1 cells ($8.4 \times 10^4$), FM3A cells ($15.4 \times 10^4$) or Meth A cells ($10.0 \times 10^4$) was suspended into RPMI 1640 medium supplemented with 10% fetal calf serum, and incubated in the air containing 5% $CO_2$ at 37° C. for 24 hours. Each culture was added with M-5 in such an amount that the final concentration would be 1 mg/ml, and further incubated under the above conditions. Every 24th hour after the incubation added with M-5, the number of viable cells was counted by Trypan blue dye exclusion.

The results are shown in Table 8.

TABLE 8

| Direct inhibitory effect against cell growth: | | | |
|---|---|---|---|
| Incubation time after the addition of the agent (hr.) | Cell number/ml | | Cell number ratio (% of the control) |
| | Control | M-5 | |
| (1) YAC-1: | | | |
| 0 | $19.3 \times 10^4$ | $19.3 \times 10^4$ | 100 |
| 24 | $56.0 \times 10^4$ | $54.3 \times 10^4$ | 97.0 |
| 48 | $109.0 \times 10^4$ | $102.5 \times 10^4$ | 94.0 |
| (2) FM3A: | | | |
| 0 | $34.9 \times 10^4$ | $34.9 \times 10^4$ | 100 |
| 24 | $57.8 \times 10^4$ | $58.1 \times 10^4$ | 100.5 |
| 48 | $114.5 \times 10^4$ | $110.8 \times 10^4$ | 96.8 |
| (3) Meth A: | | | |
| 0 | $1.64 \times 10^4$ | $1.64 \times 10^4$ | 100 |
| 24 | $3.32 \times 10^4$ | $3.29 \times 10^4$ | 99.1 |
| 48 | $5.92 \times 10^4$ | $5.78 \times 10^4$ | 97.6 |

TEST 9

Acute toxicity:

Female mice (average body weight: 23 g, 5 weeks of age) of ddy strain were used. Each group consisted of 10 mice. The physiological saline solution of M-5 was administered intravenously in a dose of 1 g (M-5)/kg-body weight. For one week after administration, the substance of the present invention did not show the inhibitory effect on body weight gain or caused no death of the mice. $LD_{50}$ of the substance of the present invention is considered to be 1 g or more/kg-body weight in the case of the intravenous administration.

TEST 10

Antigenicity:

Hartley female guinea pigs (average body weight: 350 g) were used. Each group consisted of 6 guinea pigs. By using physiological saline solution of M-5, the guinea pigs were subjected to the sensitization by the intracutaneous administration 6 times in total (3 times/week) in a dose of 1 mg (M-5)/guinea pig. Two weeks after the final sensitization, the physiological saline solution of M-5 was administered intravenouly in a dose of 10 mg (M-5)/kg-body weight or 2 mg (M-5)/kg-body weight. By observing behaviors of guinea pigs before and after the challenge, the substance of the present invention did not induce anaphylactic shock at all in the two abovementioned cases 10 mg/kg and 2 mg/kg).

TEST 11

Effect against the growth behavior of mouse normal cell:

Effect of the substance of the present invention against the growth behavior of cultured normal cells was tested by using the second culture of cells (fibroblast) derived from fetal mouse skin and muscle.

Primary culture cells were obtained from 6 littermate fetal (19 days of age) mice of SHN strain. The monolayer of the primary culture cells was subjected to trypsinization. The number of the viable cells was adjusted to $6.2 \times 10^4$ per ml of RPMI 1640 medium supplemented with 10% fetal calf serum. The medium thus obtained was subjected to the second cultivation at 37° C. in the air containing 5% $CO_2$. After 5 hours' cultivation, the medium was replaced by fresh RPMI 1640 medium in the case of control group, or in the case of test groups the medium was replaced by the RPMI 1640 medium containing M-5 of 500 µg/ml or 50 µg/ml. Then each culture was continued for 15 days. The cell growth behavior and the change of the cell form were observed by microscopy while replacing each medium 3 times for the period of 15 days. As the results, the cell growth behaviors and the cell forms of the two test groups (500 µg/ml and 50 µg/ml) were not different from those of the control group, and there was no abnormal cells.

What is claimed is:

1. Thermally-denatured deoxyribonucleic acid MD-011 derived from bacteria of genus Mycobacterium, having an antitumor activity induced by heat denaturation and the salt thereof having the following physico-chemical properties as the sodium salt:
   (1) Element analysis: C; 25.57–30.75, H: 3.80–4.75, N: 12.67–14.36, P: 7.30–8.59, Na: 3.59–5.0;
   (2) Molecular weight: 30,000–1,000,000 (Molecular weight distribution pattern as shown in FIG. 1);
   (3) Melting point: The sodium salt does not show a clear melting point;
   (4) UV absorption spectrum as shown in FIG. 2;
   (5) IR absorption spectrum as shown in FIG. 3;
   (6) Solubilities in solvents: soluble in water, insoluble in ethanol, methanol, ether or acetone;
   (7) Color reaction:
       (i) Orcinol reaction: negative to RNA fraction obtained by STS fractionation method;
       (ii) Diphenylamine reaction: positive to DNA fraction obtained by STS fractionation method;

(iii) Ninhydrin reaction: negative in a concentration of 10 μg/ml;

(iv) Anthrone reaction: negative in a concentration of 10 μg/ml;

(8) Basicity, acidity or neutrality: Aqueous solution of the sodium salt shows a pH value of 6.5–7.5;

(9) Color: white powder;

(10) Specific properties: dissolvability in water or physiological saline and a high antitumor activity provided by heating at 100° C. for 60 minutes;

(11) Base composition; guanine: 30.4, adenine: 16.9, cytosine: 30.8, thymine: 21.9 (obtained by chemical analysis);

(12) Enzyme treatment: Antitumor activity is lost by treating with deoxyribonuclease I (DNase I); Antitumor activity is not changed by treating with ribonuclease $T_2$ (RNase $T_2$);

(13) Column chromatography; Fractionation by chromatography on a column of hydroxyapatite for analyzing nucleic acid shows single-stranded structure;

(14) Transition temperature (Tm): A clear transition temperature is not able to be determined.

2. Thermally-denatured deoxyribonucleic acid MD-011 as claimed in claim 1 wherein the bacteria belonging to genus Mycobacterium is at least one member selected from the group consisting of *Mycobacterium bovis* BCG, ATCC 19015, *Mycobacterium tuberculosis* $H_{37}Ra$, ATCC 25177, *Mycobacterium smegmatis*, ATCC 607 and *Mycobacterium smegmatis*, IFO 3153.

3. An immunopotentiator comprising a pharmaceutically acceptable carrier and, as an active ingredient, thermally-denatured deoxyribonucleic acid MD-011 derived from bacteria of genus Mycobacterium, having the following physiocochemical properties as the sodium salt:

(1) Element analysis: C: 25.57–30.75, H: 3.80–4.75, N: 12.67–14.36, P: 7.30–8.59, Na: 3.59–5.0;

(2) Molecular weight: 30,000–1,000,000 (Molecular weight distribution pattern as shown in FIG. 1);

(3) Melting point: The sodium salt does not show a clear melting point;

(4) UV absorption spectrum as shown in FIG. 2;

(5) IR absorption spectrum as shown in FIG. 3;

(6) Solubilities in solvents: soluble in water, insoluble in ethanol, methanol, ether or acetone;

(7) Color reaction:
  (i) Orcinol reaction: negative to RNA fraction obtained by STS fractionation method;
  (ii) Diphenylamine reaction: positive to DNA fraction obtained by STS fractionation method;
  (iii) Ninhydrin reaction: negative in a concentration of 10 μg/ml;
  (iv) Anthrone reaction: negative in a concentration of 10 μg/ml;

(8) Basicity, acidity or neutrality: Aqueous solution of the sodium salt shows a pH value of 6.5–7.5;

(9) Color: white powder;

(10) Specific properties: dissolvability in water or physiological saline and a high antitumor activity provided by heating at 100° C. for 60 minutes;

(11) Base composition: guanine: 30.4, adenine: 16.9, cytosine: 30.8, thymine: 21.9 (obtained by chemical analysis);

(12) Enzyme treatment: Antitumor activity is lost by treating with deoxyribonuclease I(DNase I); Antitumor activity is not changed by treating with ribonuclease $T_2$ (RNase $T_2$);

(13) Column chromatography: Fractionation by chromatography on a column of hydroxyapatite for analyzing nucleic acid shows single-stranded structure;

(14) Transition temperature (Tm): A clear transition temperature is not able to be determined.

4. An immunopotentiator as claimed in claim 3 wherein the pharmaceutically acceptable carrier is at least one member selected from the group consisting of mannitol, sorbitol, maltose, dextran and squalene.

5. An immunopotentiator as claimed in claim 3 wherein the bacteria belonging to genus Mycobacterium is at least one member selected from the group consisting of *Mycobacterium bovis* BCG, ATCC 19015, *Mycobacterium tuberculosis* $H_{37}Ra$, ATCC 25177, *Mycobacterium smegmatis*, ATCC 607 and *Mycobacterium smegmatis*, IFO 3153.

* * * * *